US012616821B2

(12) United States Patent
Bunney

(10) Patent No.: US 12,616,821 B2
(45) Date of Patent: May 5, 2026

(54) ABSCESS CATHETER

(71) Applicant: Andrew Bunney, Minneapolis, MN (US)

(72) Inventor: Andrew Bunney, Minneapolis, MN (US)

( * ) Notice: Subject to any disclaimer, the term of this patent is extended or adjusted under 35 U.S.C. 154(b) by 286 days.

(21) Appl. No.: 18/380,787

(22) Filed: Oct. 17, 2023

(65) Prior Publication Data

US 2024/0123201 A1     Apr. 18, 2024

Related U.S. Application Data

(60) Provisional application No. 63/417,149, filed on Oct. 18, 2022.

(51) Int. Cl.
*A61M 27/00* (2006.01)
*A61M 3/02* (2006.01)
(Continued)

(52) U.S. Cl.
CPC .......... *A61M 27/00* (2013.01); *A61M 3/0283* (2013.01); *A61M 25/0032* (2013.01);
(Continued)

(58) Field of Classification Search
CPC ............... A61M 27/00; A61M 3/0283; A61M 25/0032; A61M 25/007; A61M 25/0097; A61M 25/0102; A61M 25/09; A61M 29/00; A61M 1/85; A61M 25/0041; A61M 25/01; A61M 25/0662; A61M 1/84; A61M 25/0023; A61M 25/10; A61M 25/0068;
(Continued)

(56) References Cited

U.S. PATENT DOCUMENTS 3,982,546 A * 9/1976 Friend ..................... A61M 1/71
604/173
4,601,713 A * 7/1986 Fuqua ............... A61M 25/0032
604/528

(Continued)

FOREIGN PATENT DOCUMENTS

DE      10-2010-045384          3/2012
DE       102010045384 A1 *  3/2012   .......... A61M 3/0283
EP           3081238 B1 *  11/2018   ............ A61M 1/774

OTHER PUBLICATIONS

Boston Scientific, "Expel: Drainage Catheter with Twist-Loc Hub," available on or before Jun. 12, 2015, retrieved on Apr. 17, 2024, retrieved from URL<https://www.bostonscientific.com/en-US/products/catheters--drainage/Expel_Drainage_Catheters.html>, 7 pages.
(Continued)

*Primary Examiner* — Rebecca E Eisenberg
*Assistant Examiner* — Brandon W. Levy
(74) *Attorney, Agent, or Firm* — Fish & Richardson P.C.

(57) ABSTRACT

System and methods for draining an abscess with a catheter. The system includes a catheter and a stiffener. The catheter has a first lumen and a second lumen. The stiffener is sized to fit inside the first lumen. The stiffener defines a channel sized to fit the second lumen such that a distal end of the stiffener can pass into and through the first lumen of the catheter with the second lumen positioned in the channel of the stiffener while the stiffener slides through the first lumen.

15 Claims, 7 Drawing Sheets

(51) Int. Cl.
     *A61M 25/00*     (2006.01)
     *A61M 25/01*     (2006.01)
     *A61M 25/09*     (2006.01)
     *A61M 29/00*     (2006.01)
(52) U.S. Cl.
     CPC ...... *A61M 25/007* (2013.01); *A61M 25/0097*
       (2013.01); *A61M 25/0102* (2013.01); *A61M*
       *25/09* (2013.01); *A61M 29/00* (2013.01)
(58) Field of Classification Search
     CPC .. A61M 1/77; A61B 18/1492; A61B 1/00154;
       A61B 17/3415; A61B 2217/005; A61B
       2217/007; A61B 17/22; A61B
       2017/22079; A61B 17/00234; A61B
       2017/003; A61B 2218/002; A61F
       2002/30677
     See application file for complete search history.

(56)         References Cited

U.S. PATENT DOCUMENTS

| | | | | | |
|---|---|---|---|---|---|
| 5,041,085 | A | * | 8/1991 | Osborne | A61M 25/01 |
| | | | | | 604/95.04 |
| 5,053,004 | A | * | 10/1991 | Markel | A61M 5/1582 |
| | | | | | 29/428 |
| 5,105,818 | A | * | 4/1992 | Christian | G01F 1/663 |
| | | | | | 600/463 |
| 2005/0171470 | A1 | * | 8/2005 | Kucklick | A61B 1/00135 |
| | | | | | 604/263 |
| 2011/0066170 | A1 | * | 3/2011 | Farnan | A61F 2/954 |
| | | | | | 623/1.23 |
| 2017/0303941 | A1 | * | 10/2017 | Eisner | A61M 25/09 |
| 2022/0218962 | A1 | | 7/2022 | Balesh et al. | |

OTHER PUBLICATIONS

Ding et al., "Innovative Continuous-Irrigation Approach for Wound Care after Deep Neck Infection Surgery: A Case Report," Int J Surg Case Rep, Mar. 2021, 80:105620, 3 pages.
Hsieh et al., "Innovative Continuous Wound Irrigation Approach for Postoperative Treatment of Masticator Space Abscess," Ear Nose Throat J., Jan. 28, 2021, 102(2):133-135.
Inari Medical, "FlowTriever System," available on or before Sep. 27, 2020, retrieved on Apr. 17, 2024, retrieved from URL<https://www.inarimedical.com/flowtriever/>, 5 pages.
Jadhav et al., "Ultrasound-Guided Pigtail Catheter Drainage: An Effective Alternative to Exploratory Laparotomy," Jan. 7, 2023, Cureus, 10 pages.

* cited by examiner

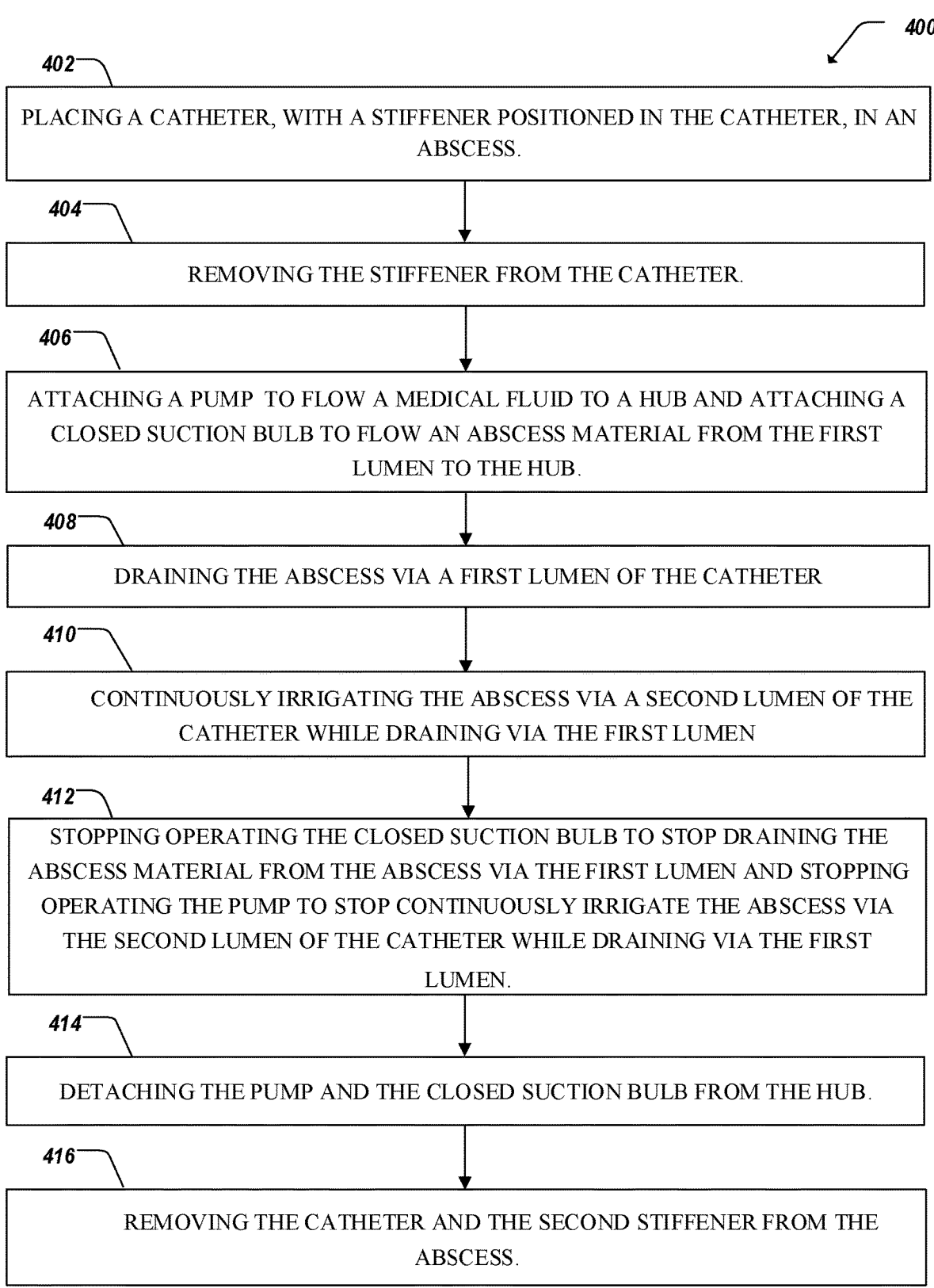

_400_

_402_

PLACING A CATHETER, WITH A STIFFENER POSITIONED IN THE CATHETER, IN AN ABSCESS.

_404_

REMOVING THE STIFFENER FROM THE CATHETER.

_406_

ATTACHING A PUMP TO FLOW A MEDICAL FLUID TO A HUB AND ATTACHING A CLOSED SUCTION BULB TO FLOW AN ABSCESS MATERIAL FROM THE FIRST LUMEN TO THE HUB.

_408_

DRAINING THE ABSCESS VIA A FIRST LUMEN OF THE CATHETER

_410_

CONTINUOUSLY IRRIGATING THE ABSCESS VIA A SECOND LUMEN OF THE CATHETER WHILE DRAINING VIA THE FIRST LUMEN

_412_

STOPPING OPERATING THE CLOSED SUCTION BULB TO STOP DRAINING THE ABSCESS MATERIAL FROM THE ABSCESS VIA THE FIRST LUMEN AND STOPPING OPERATING THE PUMP TO STOP CONTINUOUSLY IRRIGATE THE ABSCESS VIA THE SECOND LUMEN OF THE CATHETER WHILE DRAINING VIA THE FIRST LUMEN.

_414_

DETACHING THE PUMP AND THE CLOSED SUCTION BULB FROM THE HUB.

_416_

REMOVING THE CATHETER AND THE SECOND STIFFENER FROM THE ABSCESS.

FIG. 4

ABSCESS CATHETER

CLAIM OF PRIORITY

This application claims priority to U.S. Patent Application Ser. No. 63/417,149, filed on Oct. 18, 2022, the entire contents of which are hereby incorporated by reference.

TECHNICAL FIELD

This disclosure relates to treating an abscess or fluid collection, in particular, by using a catheter.

BACKGROUND

An abscess is a focal infection within an infected individual. Abscesses can occur in any organ structure and any potential space. Some abscesses occur spontaneously. Other abscesses occur when an internal organ (i.e., a colon or an intestine) containing microbial organisms (such as bacteria) ruptures and the microbial organisms leaks into an internal volume of the infected individual. The internal volume of the infected individual, for example, a peritoneum, is not designed to safely contain the microbial organisms. For example, an abscess can occur in an abdominal void as a result of appendicitis or a ruptured gallbladder.

When the microbial organisms are present in the internal volume outside the internal organ, the microbial organisms begin to multiply at an infection site (i.e., an infection). The body of the infected individual senses the presence and growth of the microbial organisms in the internal volume at the infection site. The body of the infected individual, as a defense mechanism, builds an enclosing bubble around the microbial organisms at the infection site. The enclosing bubble forms a thick wall which contains the microbial organisms at the infection site in the infected individual. The thick wall separates the microbial organisms from the rest of the body of the infected individual and a circulatory system (i.e., a bloodstream) of the infected individual. The thick wall of the enclosing bubble and the contained microbial organisms are the abscess.

Sometimes, an immune system of the infected individual is not strong enough to overcome a growth rate of the microbial organisms in the abscess. When this occurs, the microbial organisms can overpopulate the abscess, leading the microbial organisms to invade the bloodstream of the infected individual. The release of the microbial organisms into the blood stream can cause sepsis in the infected individual. Sepsis is a life-threatening condition which, if untreated, can lead to a multi-system organ failure and death.

SUMMARY

This disclosure describes systems and methods related to treating an abscess using a catheter. This approach can simultaneously drain and irrigate the abscess with the catheter. The catheter can have two lumens—a first lumen and a second lumen. The second lumen can be positioned inside the first lumen. The abscess can be drained via the first lumen and simultaneously irrigated via the second lumen while draining via the first lumen.

In one aspect, a system for draining an abscess includes a catheter and a stiffener. The catheter has a first lumen and a second lumen. The stiffener is sized to fit inside the first lumen. The stiffener defines a channel sized to fit the second lumen such that a distal end of the stiffener can pass into and through the first lumen of the catheter with the second lumen positioned in the channel of the stiffener while the stiffener slides through the first lumen.

In some implementations, the catheter defines a first lumen inlet at a distal end of the catheter. The stiffener defines a dilator at a distal end of the stiffener. The stiffener is sized such that the dilator extends out of the first lumen inlet when the catheter and dilator are combined to be inserted into a patient. In some cases, the second lumen further includes a second lumen outlet at the distal end of the catheter and the first lumen inlet and the second lumen outlet are coplanar. In some cases, the first lumen inlet is farther from a proximal end than a second lumen outlet. In some cases, a second lumen outlet is farther from the proximal end than the first lumen inlet. In some cases, a diameter of the first lumen inlet is 0.035 inches.

In some implementations, the stiffener defines a guidewire passage in a center of the stiffener and the channel is defined along a perimeter edge of the stiffener.

In some implementations, the second lumen is positioned inside the first lumen.

In some implementations, the second lumen is coupled to an interior surface of the first lumen.

In some implementations, a wall of the first lumen further includes multiple side holes.

In some implementations, a wall of the catheter that defines the first lumen has multiple side holes.

In some implementations, the catheter further includes multiple voids extending from the first lumen through an outer wall to a space exterior of the first lumen.

In some implementations, the catheter further includes a first lumen outlet at a proximal end of the catheter and a second lumen inlet at the proximal end of the catheter. In some cases, the system further includes a hub positioned at the proximal end of the catheter. The hub includes an inlet conduit coupled to the second lumen inlet and an outlet conduit coupled to the first lumen outlet. Sometimes, the system further includes a lock coupled to the hub. Sometimes, the lock can include multiple hinged wire loops. Sometimes, the lock includes Leur-lock adaptors.

In some implementations, a portion of the catheter conforms to a C-shape responsive to a removal of the stiffener. In some implementations, a portion of the catheter conforms to a spiral shape responsive to a removal of the stiffener. In some cases, the portion is at the distal end of the catheter.

In some implementations, a diameter of the first lumen is between eight at twenty-six Fr and a diameter of the second lumen is between three and four Fr.

In some implementations, the system includes a tip coupled to and extending from the distal end of the first lumen. The tip narrows to a diameter of 0.035 inches.

In some implementations, the system further includes a hydrophilic coating on an outer surface of the catheter.

In some implementations, the catheter is a poly-urethane material.

In another aspect, an abscess draining kit includes a catheter, a stiffener, and a catheter removal mechanism. The catheter has a first lumen and a second lumen. The second lumen is positioned within the first lumen. The stiffener has a channel. The stiffener is sized to slide through the first lumen while the second lumen slides through the channel.

In some implementations, the catheter removal mechanism straightens the catheter.

In some implementations, the catheter removal mechanism is at least one of another stiffener or a suture mediated lock.

In some implementations, the abscess draining kit includes an intravenous pump.

In some implementations, the abscess draining kit includes a closed suction bulb.

In some implementations, the abscess draining kit includes a medical fluid. In some cases, the medical fluid is at least one of a saline solution, an antibiotic medicine, or a tissue plasminogen activase solution.

In another aspect, a catheter defines a drainage lumen for draining an abscess and an irrigation lumen for irrigating the abscess. The irrigation lumen is positioned at a perimeter of the drainage lumen.

In some implementations, the catheter further includes multiple voids extending from the drainage lumen to a space exterior of the drainage lumen.

In some implementations, the voids are sized to flow an abscess fluid and an abscess material.

In some implementations, the drainage lumen further includes a drainage lumen inlet positioned at a distal end of the catheter.

In some implementations, the drainage lumen further includes a drainage lumen inlet positioned between a distal end and a proximal end of the catheter.

In some implementations, the drainage lumen further includes a drainage lumen inlet positioned at a proximal end of the catheter.

In some implementations, the irrigation lumen further includes an irrigation lumen outlet positioned at a distal end of the catheter.

In some implementations, the drainage lumen further includes a drainage lumen inlet positioned at a distal end of the catheter, the irrigation lumen further includes an irrigation lumen outlet positioned at the distal end of the catheter, and the drainage lumen inlet and the irrigation lumen outlet are substantially coplanar.

In some implementations, the drainage lumen is sized to allow a stiffener to pass from a proximal end to a distal end of the catheter.

In some cases, the irrigation lumen is sized to slide through a channel of the stiffener as the stiffener passes from the proximal end to the distal end of the catheter.

In some implementations, the catheter further includes a hub coupled to the drainage lumen and the irrigation lumen. The hub flows a medical fluid into the irrigation lumen and flows an abscess fluid from the drainage lumen.

In yet another aspect, a catheter defines a drainage lumen for draining an abscess and an irrigation lumen for irrigating the abscess. The irrigation lumen is positioned inside of the drainage lumen.

In some implementations, the catheter further includes multiple voids extending from the drainage lumen to a space exterior of the drainage lumen.

In some implementations, the voids are sized to flow an abscess fluid and an abscess material.

In some implementations, the drainage lumen further includes a drainage lumen inlet positioned at a distal end of the catheter.

In some implementations, the drainage lumen further includes a drainage lumen inlet positioned between a distal end and a proximal end of the catheter.

In some implementations, the drainage lumen further includes a drainage lumen inlet positioned at a proximal end of the catheter.

In some implementations, the irrigation lumen further includes an irrigation lumen outlet positioned at a distal end of the catheter.

In some implementations, the drainage lumen further includes a drainage lumen inlet positioned at a distal end of the catheter. The irrigation lumen further includes an irrigation lumen outlet positioned at the distal end of the catheter. The drainage lumen inlet and the irrigation lumen outlet are substantially coplanar.

In some implementations, the drainage lumen is sized to allow a stiffener to pass from a proximal end to a distal end of the catheter. In some cases, the irrigation lumen is sized to slide through a channel of the stiffener as the stiffener passes from the proximal end to the distal end of the catheter.

In some implementations, the catheter further includes a hub coupled to the drainage lumen and the irrigation lumen. The hub flows a medical fluid into the irrigation lumen and flows an abscess fluid from the drainage lumen.

In another aspect, a catheter defines an axis extending from a proximal end to a distal end of the catheter. The catheter defines a drainage lumen for draining an abscess and an irrigation lumen for irrigating the abscess. The drainage lumen terminates at a distal drainage opening and the irrigation lumen terminates a distal irrigation opening. The distal drainage opening and the distal irrigation opening are located at substantially a same axial location along the axis of the catheter.

In some implementations, the distal irrigation opening is positioned inside the distal drainage opening at a perimeter of the distal drainage opening.

In another aspect, a catheter defines a drainage lumen for draining an abscess and an irrigation lumen for irrigating the abscess. The catheter defines a first set drainage holes positioned circumferentially about the drainage lumen at a first axial location and a second set of drainage holes positioned circumferentially about the drainage lumen at a second axial location different than the first axial location.

In another aspect, a system for draining an abscess includes a catheter, a negative pressure source, and an irrigation source. The catheter is sized for percutaneous use in draining the abscess. The catheter defines a drainage lumen and an irrigation lumen. The negative pressure source can be connected to the drainage lumen at a proximal end of the catheter. The irrigation source can be connected to the irrigation lumen at the proximal end of the catheter. The irrigation source irrigates the abscess while the negative pressure source operates to drain the abscess.

In some implementations, the system further includes a stiffener. The stiffener is sized to fit inside the drainage lumen about the irrigation lumen and allow a channel of the stiffener to pass about the irrigation lumen as the stiffener passes into and through the drainage lumen.

In some implementations, the stiffener further includes a guidewire passage and the system further includes a guidewire to engage the guidewire passage to couple to the stiffener.

In yet another aspect, an abscess is treated by draining the abscess via a first lumen of a catheter and continuously irrigating the abscess via a second lumen of the catheter while draining via the first lumen.

In some implementations, draining the abscess includes receiving an abscess material from a space exterior the first lumen through multiple voids into the first lumen.

In some implementations, treating the abscess includes flowing a medical fluid out of a second lumen outlet of the second lumen to irrigate the abscess and receiving one or more of a medical fluid and an abscess material at a first lumen inlet of the first lumen. The second lumen outlet and the first lumen inlet are coplanar.

In some implementations, before draining and continuously irrigating the abscess, treating the abscess includes placing the catheter, with a stiffener positioned in the catheter, in the abscess. The stiffener is sized to fit inside the first lumen. The stiffener defines a channel sized to fit the second lumen such that a distal end of the stiffener can pass into and through the first lumen of the catheter with the second lumen positioned in the channel of the stiffener while the stiffener slides through the first lumen.

In some implementations, after placing the catheter and the stiffener in the abscess, treating the abscess includes removing the stiffener from the catheter. In some cases, removing the stiffener from the catheter allows a portion of the catheter to relax to form a C-shape. In some cases, removing the stiffener from the catheter allows a portion of the catheter to relax to form a spiral shape. In some cases, removing the stiffener from the catheter engages the catheter to the abscess. In some cases, the catheter includes a hub coupled to the first lumen and the second lumen. The hub conducts the medical fluid into the first lumen and an abscess material from the first lumen. After removing the stiffener from the catheter, treating the abscess includes attaching a pump to flow the medical fluid to the hub and attaching a closed suction bulb to flow the abscess material from the first lumen to the hub.

In some implementations, treating the abscess includes operating the closed suction bulb to drain the abscess material from the abscess via the first lumen and operating the pump to continuously irrigate the abscess via the second lumen of the catheter while draining via the first lumen.

In some implementations, treating the abscess includes further stopping operating the closed suction bulb to stop draining the abscess material from the abscess via the first lumen and stopping operating the pump to stop continuously irrigate the abscess via the second lumen of the catheter while draining via the first lumen. In some cases, treating the abscess includes detaching the pump and the closed suction bulb from the hub.

In some implementations, the stiffener is a first stiffener. Treating the abscess includes inserting a second stiffener into the catheter. The second stiffener is sized to fit inside the first lumen. The second stiffener defines a second channel sized to fit the second lumen such that a distal end of the second stiffener can pass into and through the first lumen of the catheter with the second lumen positioned in the second channel of the second stiffener while the second stiffener slides through the first lumen. In some cases, inserting the second stiffener into the catheter straightens a portion of the catheter. In some cases, inserting the second stiffener into the catheter disengages the catheter from the abscess. In some cases, treating the abscess includes removing the catheter and the second stiffener from the abscess.

In some implementations, after draining the abscess via a first lumen of a catheter and continuously irrigating the abscess via the second lumen of the catheter while draining via the first lumen, treating the abscess includes plugging the second lumen of the catheter to prevent fluid flow through the second lumen of the catheter while draining the abscess via the first lumen. In some cases, treating the abscess includes attaching a second closure suction bulb the hub to drain the abscess via the first lumen and draining the abscess via the first lumen of the catheter to the closure suction bulb. In some cases, treating the abscess includes unplugging the second lumen of the catheter to allow fluid flow through the second lumen of the catheter while draining the abscess via the first lumen. In some cases, treating the abscess includes attaching the pump to flow the medical fluid to the hub and after attaching the pump to the hub, simultaneously operating the closed suction bulb to drain the abscess material from the abscess via the first lumen and operating the pump to continuously irrigate the abscess via the second lumen of the catheter while draining via the first lumen.

Implementations of the present disclosure can realize one or more of the following advantages. These systems and methods can increase a removal rate of the microbial organisms, infected tissue, and inflammatory material from the abscess to outside the infected individual. For example, large side holes and a high number of side holes can drain (flow) the microbial organisms, infected tissue, and inflammatory material from the abscess into the first lumen (i.e., a drainage lumen) which can increase the removal rate of the microbial organisms, infected tissue, and inflammatory material from the abscess to outside the infected individual. For example, flowing a medical fluid such as a sterile saline solution through the second lumen into the abscess can increase a pressure of the abscess or induce the flow of microbial organisms, infected tissue, and inflammatory material entrained with the medical fluid from the abscess to outside the infected individual. In some cases, a medical device such as an intravenous pump can be coupled to the second lumen to increase the pressure of the medical fluid flowing through the second lumen to the abscess. For example, reducing a pressure in the first lumen via a closed suction bulb can induce the flow of the microbial organisms, infected tissue, and inflammatory material from the abscess to outside the infected individual. For example, medical fluids such as a tissue plasminogen activase (tPA) solution can be flowed into the abscess. The tPA solution can increase the breakup of organized partially necrotic tissue in the abscess, thus increasing the removal rate of the microbial organisms infected tissue, and inflammatory material from the abscess to outside the infected individual.

These systems and methods can decrease a treatment time for the infected individual. For example, continuously irrigating the abscess can increase thinning and dilution of the microbial organisms, infected tissue, and inflammatory biological material, allowing the microbial organisms, infected tissue, and inflammatory biological material to more easily flow from the abscess to outside the infected individual, thus decreasing the treatment time needed for the infected individual. For example, continuously irrigating the abscess can reduce settling, clumping, and hardening of infected tissue, and inflammatory biological material and liquids in the abscess, allowing the microbial organisms, infected tissue, and inflammatory biological material to flow from the abscess to outside the infected individual, thus decreasing the treatment time needed for the infected individual.

These systems and methods can decrease the growth rate of microbial organisms in the infected individual. For example, medical fluids such as an antibiotic medicine can be flowed into the abscess along with the saline solution. The antibiotic medicine can reduce the growth rate of the microbial organisms in the abscess.

These systems and methods can increase safety for the infected individual. For example, the hub connecting the first lumen to the closed suction bulb and the second lumen to the intravenous pump can eliminate the use of a three-way valve. The three-way valve, which is standard in current treatment regimens, can be operated to flow medical fluids from medical devices through catheters and alternately to flow microbial organisms, infected tissue, and inflammatory biological material out of the abscess. Sometimes, the three-way valve could be operated incorrectly, harming the infected individual. Using the hub instead of requiring a separate three-way valve to control the flow of medical fluids and abscess material can increase safety for the infected individual.

For example, actuating some three-way valves repeatedly can result in a mechanical failure such as a crack or excessive wear, resulting in leaking medical fluid or abscess fluid outside the system and back onto the infected individual, a medical professional, or a medical treatment facility, contaminating the surrounding environment or the infected individual. For example, an internal conduit of the three-way valve is smaller compared to the first lumen and an outlet conduit of the hub. The internal conduit of the three-way valve can become clogged with abscess material. When the three-way valve is clogged, the flow rate of abscess material from the abscess can decrease or stop, harming the infected individual. A medical professional may need to intervene and clean, unclog, or replace the three-way valve to restore drainage of the abscess and treatment of the infected individual. Replacing a single lumen catheter having the three-way valve with the two lumen abscess catheter having the hub described herein can increase safety for the infected individual.

The details of one or more implementations of the subject matter described in this disclosure are set forth in the accompanying drawings and the description below. Other features, aspects, and advantages of the subject matter will become apparent from the description, the drawings, and the claims.

BRIEF DESCRIPTION OF THE DRAWINGS

FIG. 4 is a flow chart of an example method of continuously irrigating an abscess with a catheter according to the implementations of the present disclosure.

DETAILED DESCRIPTION

The present disclosure relates to treating an abscess with a catheter. The catheter is placed in an abscess of an infected individual to drain and to continuously irrigate the abscess. The catheter has a first lumen and a second lumen. The second lumen is positioned inside the first lumen. A stiffener is placed inside the first lumen. The stiffener has a channel sized to fit about second lumen such that a distal end of the stiffener can pass into and through the first lumen of the catheter with the second lumen positioned in the channel of the stiffener while the stiffener slides through the first lumen. The catheter can be used for simultaneously irrigating and collecting fluids from the infected individual.

The stiffener is used to provide rigidity for the catheter when the catheter is placed in the abscess. Then, the stiffener is removed from the infected individual, while a distal end of the catheter remains in the abscess. The abscess is treated by draining the abscess via the first lumen and simultaneously irrigating the abscess via the second lumen while draining the abscess via the first lumen.

Figure 1A:
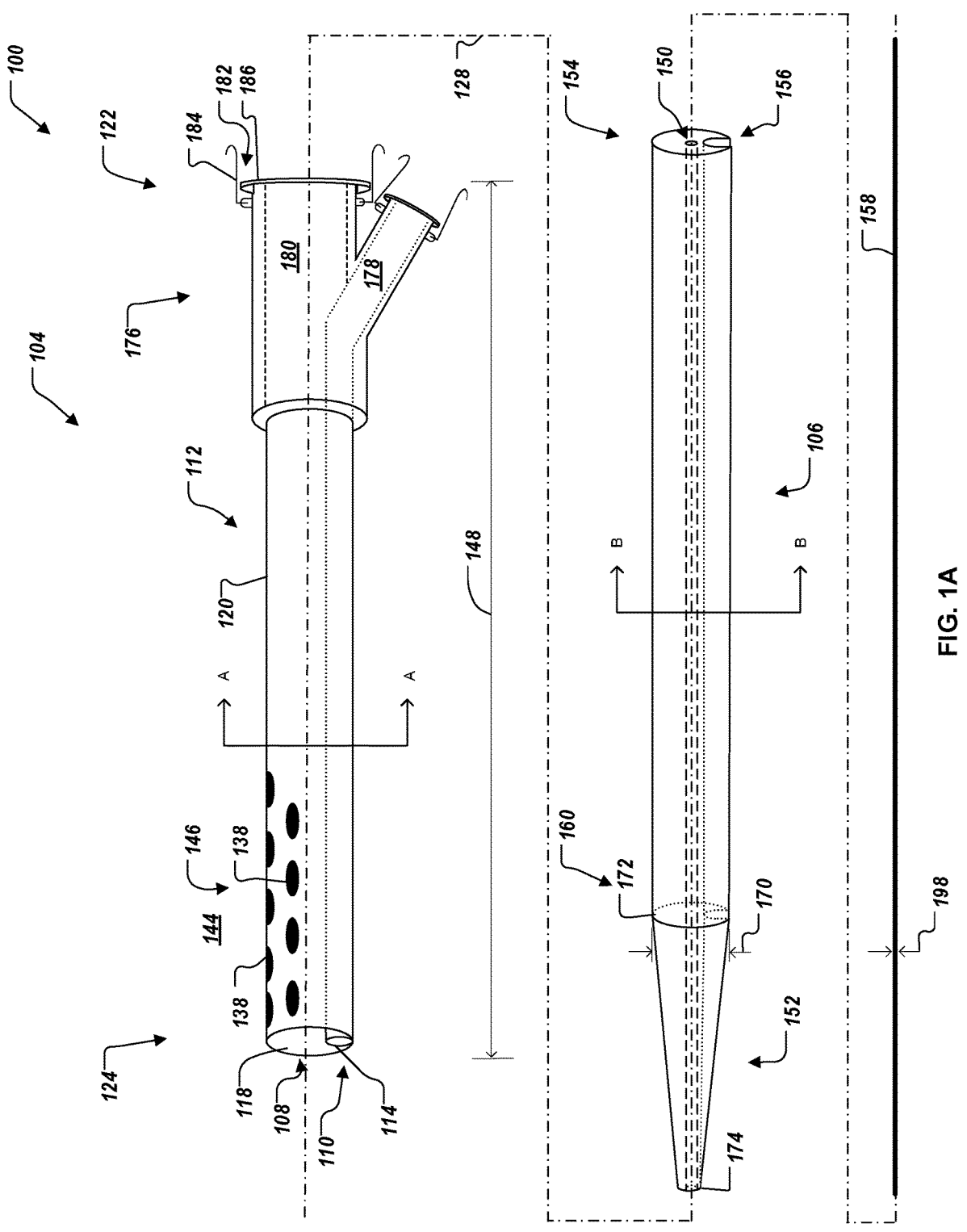
FIG. 1A is a schematic view of a system for continuously irrigating an abscess.

FIG. 1A is a schematic view of a system for continuously irrigating an abscess. FIG. 1D is a schematic view of the catheter and the stiffener of FIG. 1A positioned in an abscess. A system 100 for continuously irrigating an abscess 102 (shown in FIG. 1D) or other fluid collection of an infected individual 126 (such as a mammalian subject, shown in FIG. 1D, also known as a patient) includes a catheter 104 and a stiffener 106. The abscess 102 is filled with microbial organisms, infected tissue, and inflammatory biological material 116. The microbial organisms, infected tissue, and inflammatory biological material 116 can be a liquid, a solid, or a mixture of liquids and solids. The microbial organisms, infected tissue, and inflammatory biological material 116 can also be referred to as an abscess material.

The catheter 104 is placed in the abscess 102 by the stiffener 106 and then the stiffener 106 is removed from the catheter 104, leaving the catheter 104 in the abscess 102. Referring to FIG. 1A, the catheter 104 has a first lumen 108 (a drainage lumen) and a second lumen 110 (an irrigation lumen). When the catheter 104 is in place in the abscess 102, the first lumen 108 drains the microbial organisms, infected tissue, and inflammatory biological material 116 from the abscess 102. The second lumen 110 flows a medical fluid into the abscess 102. Draining the abscess 102 via the first lumen 108 and simultaneously flowing (continuously irrigating) the abscess 102 via the second lumen 110 treats the abscess 102. While the system 100 (including the catheter 104) can facilitate continuous irrigation and is described herein as performing continuous irrigation, some embodiments of the system 100 can perform irrigation less than continuously. For example, in some embodiments the system 100 can perform irrigation intermittently. Additionally, in some embodiments the system 100 can perform irrigation continuously during a portion of a drainage process yet can pause irrigation for another portion of the drainage process.

Figure 1B:
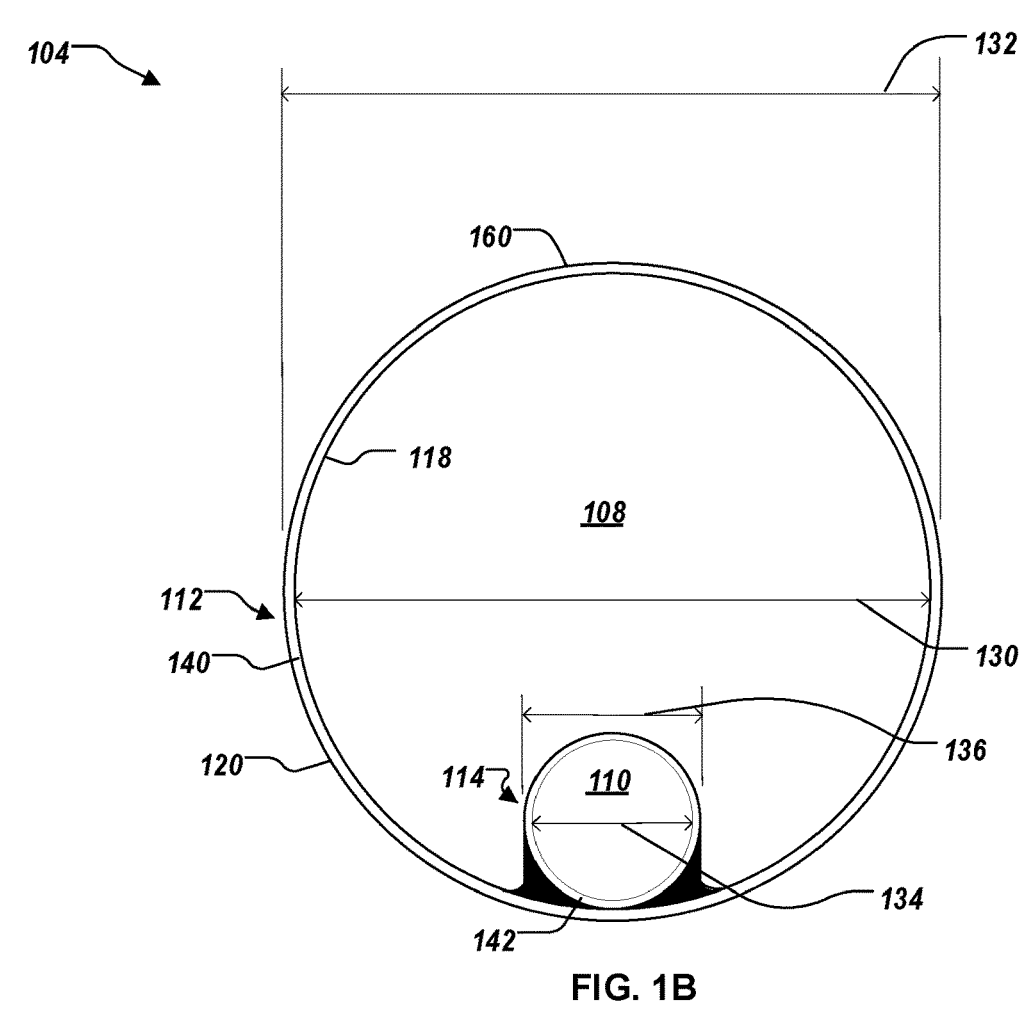
FIG. 1B is a cross-sectional view of the catheter of FIG. 1A.

FIG. 1B is a cross-sectional view of the catheter of FIG. 1A. Referring to FIGS. 1A and 1B, the second lumen 110 is inside the first lumen 108 proximate a perimeter of the first lumen 108. The first lumen 108 is defined by a first tube 112. In other words, the first lumen 108 is an interior void of the first tube 112 defined by a wall 140 (shown in FIG. 1B). The second lumen 110 is defined by a second tube 114. In other words, the second lumen 110 is an interior void of the second tube 114 defined by a wall 142 (shown in FIG. 1B). The second tube 114 is inside the first tube 112. As shown in FIG. 1A, the second tube 114 is coupled to the first tube 112. For example, the second tube 114 can contact an inner surface 118 of the wall 140 of the first tube 112. However, in other implementations, the second tube 114 is placed in a channel (not shown) on an outer surface 120 of the first tube 112. Alternatively, the second tube 114 can be suspended away (not shown) from the inner surface 118 of the first tube 112.

The first tube 112 and the second tube 114 can be constructed from a flexible and kink-resistant material. For example, the first tube 112 and the second tube 114 can be polyurethane. In some cases, the first tube 112 and the second tube 114 are radiopaque (i.e., able to be visualized with an x-ray and/or computed tomography imaging).

Figure 1C:
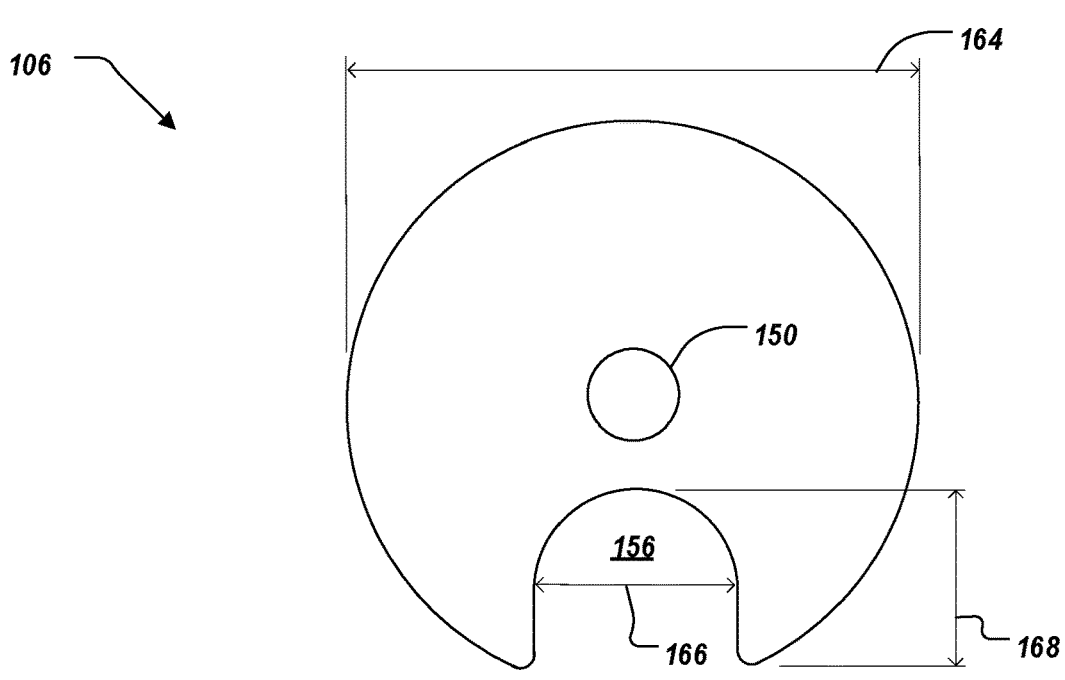
FIG. 1C is a cross-sectional view of the stiffener of FIG. 1A.
Figure 1D:
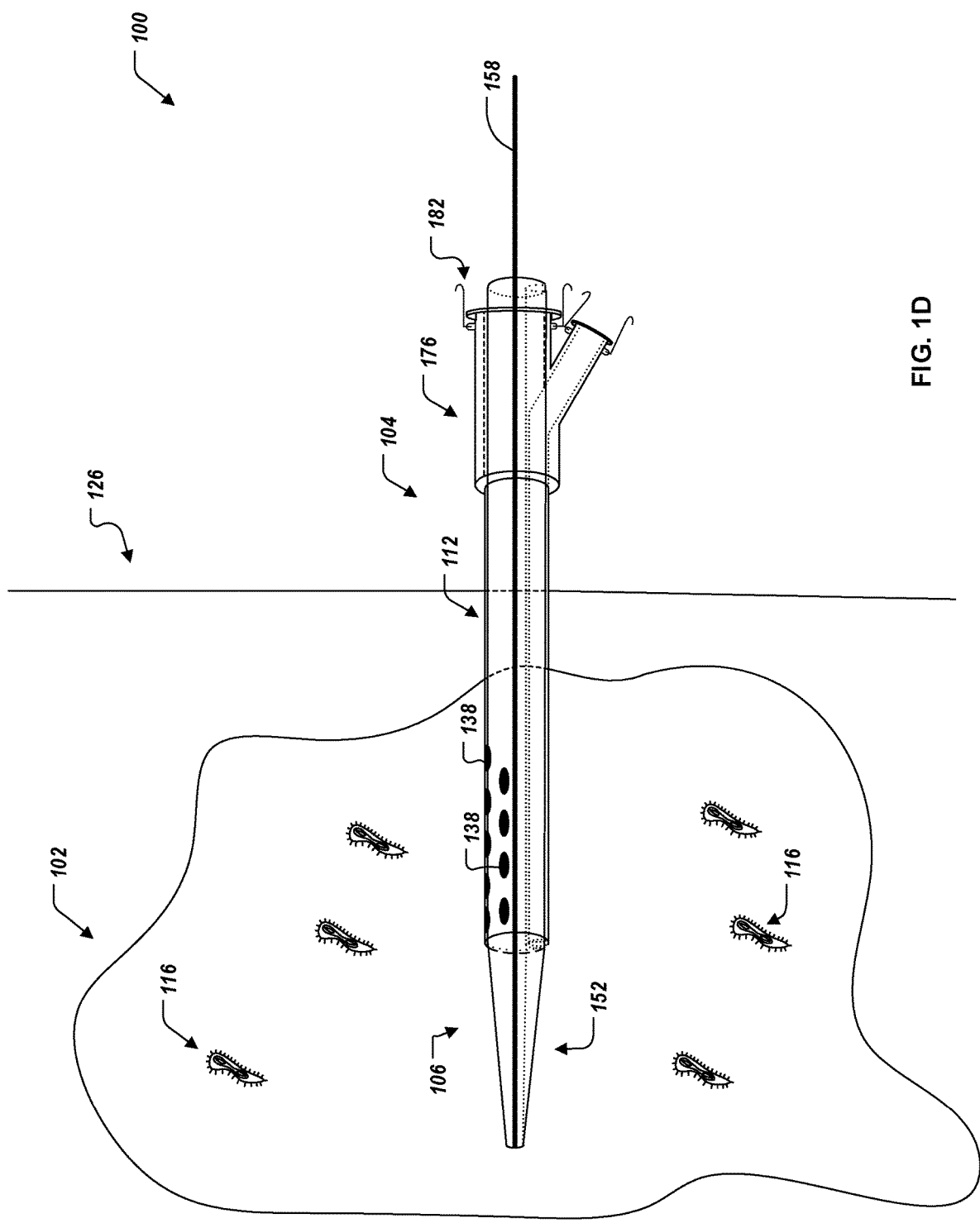
FIG. 1D is a schematic view of the catheter and the stiffener of FIG. 1A positioned in an abscess.
Figure 1E:
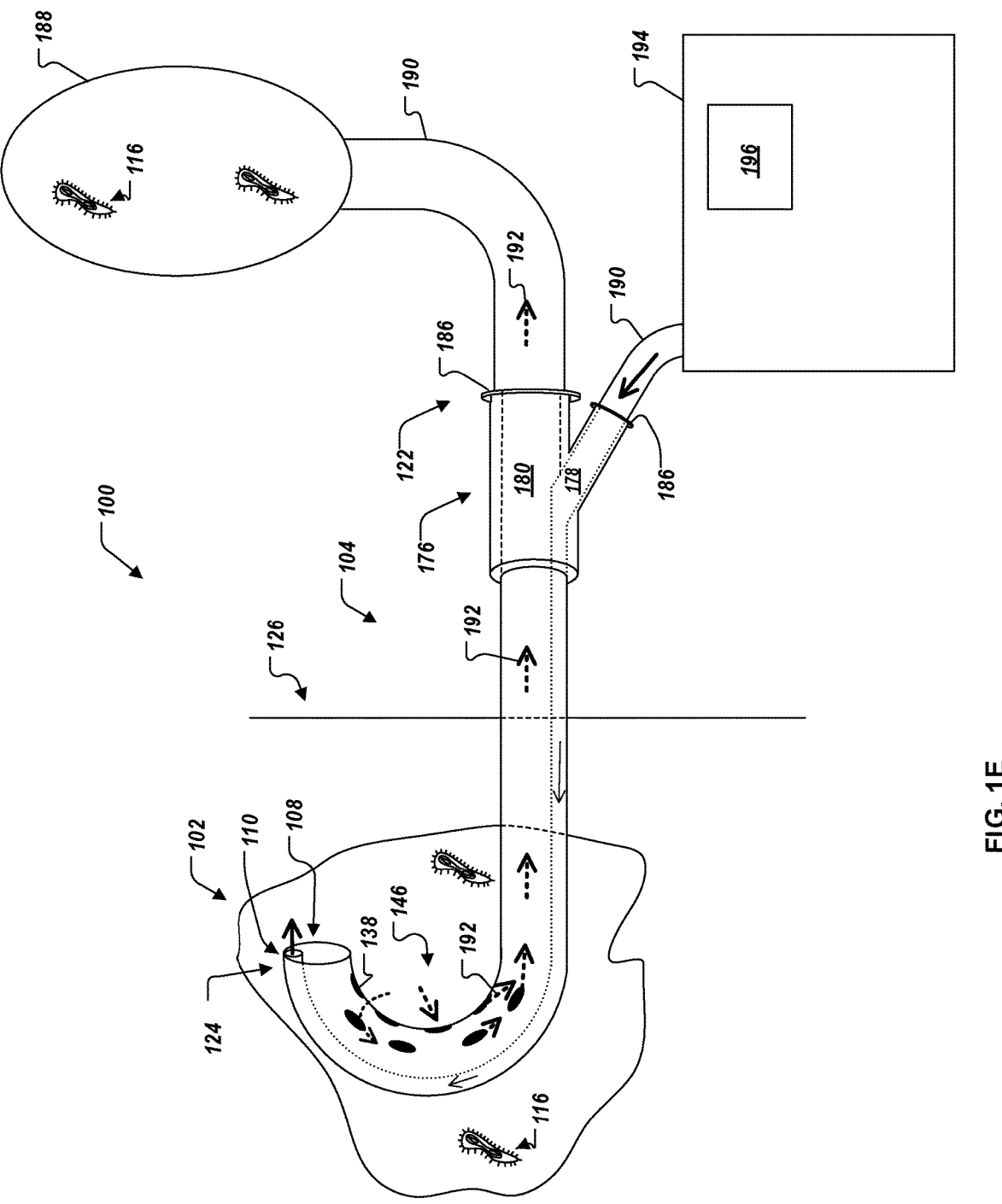
FIG. 1E is a schematic view of the catheter placed in the abscess.
Figure 3:
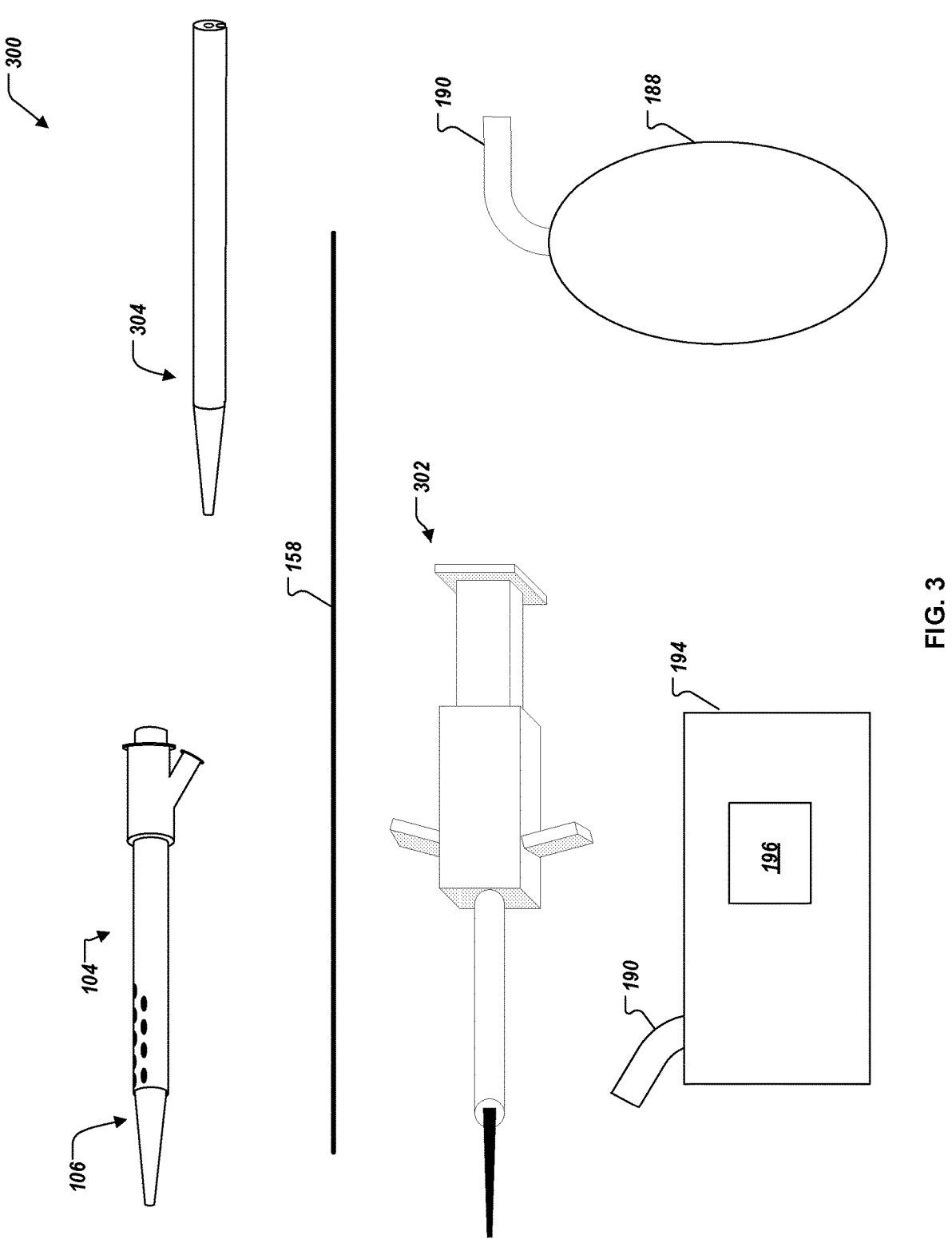
FIG. 3 is a schematic view of an abscess draining kit.

FIG. 1E is a schematic view of the system 100 with the catheter 104 placed in the abscess 102. Referring to FIG. 1E and FIG. 3, the catheter 104 has a proximal end 122 and a distal end 124. The proximal end 122 is the end that is closest to a medical professional (not shown) or other medical devices (described in reference to FIG. 1E and FIG. 3). The distal end 124 of the catheter 104 is the end that is farthest from the medical professional (not shown) or other medical devices (described in reference to FIG. 1E and FIG. 3). The distal end 124 is the end of the catheter 104 that is placed in the abscess 102 of the infected individual 126. The first lumen 108 and the second lumen 110 extend from the proximal end 122 to the distal end 124.

The proximal end 122 of the first lumen 108 defines an outlet of the first lumen 108. The distal end 124 of the first lumen 108 defines an inlet. In other words, the microbial organisms, infected tissue, and inflammatory biological material 116 drain from the abscess 102 into the first lumen 108 through the distal end 124 of the first lumen 108. The microbial organisms, infected tissue, and inflammatory biological material 116 flow through the first lumen 108 and out the proximal end 122 of the first lumen 108.

The proximal end 122 of the second lumen 110 is an inlet of the second lumen 110. The distal end 124 of the second lumen 110 is an outlet. In other words, the medical fluids 196 (described in more detail in reference to FIG. 1E) flow into the second lumen 110 through the proximal end 122 of the second lumen 110 and into the second lumen 110. The medical fluids 196 flow through the second lumen 110 and out the distal end 124 into the abscess 102 to continually irrigate the abscess 102.

As shown in FIG. 1A, the inlet of the first lumen 108 and the outlet of the second lumen 110 are co-planar. In other words, the inlet of the first lumen 108 and the outlet of the second lumen 110 are substantially aligned. That is, the inlet of the first lumen 108 and the outlet of the second lumen 110 are at the same axial location with respect to a center axis 128 of the catheter 104. The outlet of the second lumen 110 is spaced radially outward from the center axis 128.

In other implementations, not shown, the second lumen 110 can extend beyond the first lumen 108 along the distal end 124. That is, the inlet of the first lumen 108 and the outlet of the second lumen 110 are at different axial locations along the center axis 128 of the catheter 104. The outlet of the second lumen 110 can be further from the proximal end 122 than the inlet of the first lumen 108 along the center axis 128 of the catheter 104. In still other implementations, the first lumen 108 can extend beyond the second lumen 110 such that the second lumen 110 terminates inside of the first lumen 108.

FIG. 1B is a cross-sectional view of the catheter of FIG. 1A. Referring to FIGS. 1A and 1B, the first tube 112 defining the first lumen 108 has an inner diameter 130 and an outer diameter 132. For example, the outer diameter 132 of the first tube 112 can be between 8 Fr and 26 Fr. The inner diameter 130 is sized to accept the stiffener 106.

The second tube 114 defining the second lumen 110 has an inner diameter 134 and an outer diameter 136. For example, the outer diameter 136 of the second lumen 110 can be between 3 Fr and 4 Fr.

The inner diameter 130 of the first tube 112 is larger than the outer diameter 136 of the second lumen 110. The inner diameter 130 of the first tube 112 is sized so that the stiffener 106 can pass into and through the first lumen 108 from the proximal end 122 to and out of the distal end 124 of the catheter 104.

The catheter 104 has multiple side holes 138 (also referred to as voids or drain holes) in the wall 140 of the first tube 112 to conduct the flow of the microbial organisms, infected tissue, and inflammatory biological material 116 from the abscess 102 into the first lumen 108. The side holes 138 extend from the first lumen 108 through the wall 140 of the first tube 112 to a space 144 exterior of the first lumen 108. In other words, the side holes 138 extend from outer surface 120 in contact with the space 144 exterior of the first tube 112 through the wall 140 of the first tube 112 and into the first lumen 108.

The side holes 138 are shaped and sized to allow the flow of the microbial organisms, infected tissue, and inflammatory biological material 116 from the abscess 102 into the first lumen 108. For example, the side holes 138 can be circular or oval-shaped. When the side holes 138 are circular, the side holes 138 can have a diameter of between one millimeter and thirty millimeters. When the side holes 138 are oval-shaped, the side holes 138 can have a major diameter of between one millimeter and thirty millimeters and a minor diameter of between one millimeter and twenty-five millimeters.

The side holes 138 can cover a portion 146 (described in more detail below in reference to FIGS. 1A, 1D, and 1E) of the first tube 112. In some implementations, the side holes 138 cover some, most, or all of the first tube 112. In some implementations, there are between one and six, or even more, side holes extending through the first tube 112 to flow of the microbial organisms, infected tissue, and inflammatory biological material 116 from the abscess 102 into the first lumen 108.

The side holes 138 have an inner surface (not shown). The inner surface can be one or more of rounded, flat, angled, or curved. A shape of the inner surface of the side holes 138 can increase the flow rate of the microbial organisms, infected tissue, and inflammatory biological material 116 from the abscess 102 into the first lumen 108.

The catheter 104 has a length 148. In some cases, the length 148 of catheter 104 is between fifteen and forty-five centimeters.

The catheter 104, and specifically the first tube 112, has a hydrophilic coating 162 (shown in FIG. 1 B) on the outer surface 120 of the first tube 112. For example, the hydrophilic coating 162 can be a polymer. The hydrophilic coating 162 can attract water to increase the lubrication of the catheter 104. The hydrophilic coating 162 can allow for easier insertion of the catheter 104 through infected individual 126.

Referring to FIGS. 1A, 1D, and 1E, the portion 146 of the catheter 104 conforms to a C-shape (as shown in FIG. 1E) when the stiffener 106 is removed from the catheter 104. This can be referred to as a pigtail. When the portion 146 of the catheter 104 forms the C-shape, the catheter 104 can engage within the abscess 102 to help retain the catheter 104 in the abscess. The removal of the stiffener 106 releases the portion 146 to contract to form the C-shape. The C-shaped portion 146 is at the distal end 124 of the catheter 104. Accordingly, the C-shape can be the natural shape of the portion 146 of the catheter 104 when not acted on by the stiffener 106 (or other forces). In other cases, not shown, the portion 146 conforms to a pig-tail shape or a spiral shape when the stiffener 106 is removed from the catheter 104. In some cases, the portion 146 can be moved, actuated, or forced to change shape responsive to operation of a suture mediated locking mechanism by the medical professional as described in more detail in reference to FIG. 3.

FIG. 1C is a cross-sectional view of the stiffener of FIG. 1A. Referring to FIGS. 1A and 1C, the stiffener 106 fits inside the catheter 104 to place the catheter 104 in the abscess 102. In other words, the stiffener 106 straightens the catheter 104 for placement in the abscess 102. The stiffener 106 can be substantially solid except to define a guidewire passage 150 and a channel 156. The stiffener 106 defines a dilator 152 at a distal end of the stiffener. A guidewire 158 can pass through to the guidewire passage 150 from a proximal end 154 of the stiffener 106 to the distal end 160 of the dilator 152.

The proximal end 154 of the stiffener 106 is the end that is closest to the medical professional (not shown). The distal end 160 of the stiffener 106 is the end that is farthest from the medical professional (not shown). The distal end 160 is the end of the stiffener 106 that is placed in the catheter 104 to provide rigidity to the catheter 104 as the catheter 104 is inserted into the abscess 102 of the infected individual 126. The distal end 160 of the stiffener 106 straightens the portion 146 of the catheter 104, forcing the catheter 104 into a liner shape as opposed to the C-shape.

The stiffener 106 is sized to fit inside the first lumen 108. Referring to FIG. 1C, the stiffener 106 has an outer diameter 164. The outer diameter 164 of the stiffener 106 is smaller than the inner diameter 130 of the catheter 104 by an amount sufficient to allow the stiffener 106 to pass through the catheter 104. The outer diameter 164 of the stiffener 106 can be variable and size to accommodate movement of the stiffener 106 relative to the first tube 112 and within the first lumen 108.

Referring to FIGS. 1A and 1C, the channel 156 fits about the second tube 114 of the second lumen 110. The channel 156 extends from the proximal end 154 of the stiffener 106 to the distal end 160 of the stiffener 106. The channel 156 terminates on the dilator 152. The channel 156 is sized to fit the second lumen 110 such that the distal end 160 of the stiffener 106 can pass into and through the first lumen 108 of the catheter 104 with the second lumen 110 positioned in the channel 156 while the stiffener 106 slides through the first lumen 108. Referring to FIG. 1C, the channel 156 has a diameter 166 (also referred to as a width). The diameter 166 of the channel 156 is greater than the outer diameter 136 of the second tube 114. The channel 156 also has a height 168. In some cases, the height 168 is greater than the diameter 166 (the width) to ensure the stiffener 106 can pass over the second tube 114. When the channel 156 is in the stiffener 106, the height 168 and width are generally constant.

The dilator 152 is coupled to the distal end 160 of the stiffener 106. The dilator 152 extends from the distal end 160 of the stiffener 106. When the stiffener 106 is positioned in the catheter 104, the dilator 152 extends from the distal end 124 of the catheter 104. In other words, the distal end 160 of the stiffener 106 is farther from the proximal ends 122 and 154 than the distal end 124 of the catheter 104.

Referring to FIG. 1A, the dilator 152 has an outer diameter 170. The dilator 152 has a proximal end 172 coupled to the stiffener 106 and a distal end 174 farther from the proximal end 154 of the stiffener 106 along the center axis 128 than the proximal end 172. Referring to FIGS. 1A and 1B, the outer diameter 170 of the proximal end 172 of the dilator 152 is the smaller than the inner diameter 130 of the first tube 112. The outer diameter 170 of the dilator 152 decreases between the proximal end 172 and the distal end 174. That is, the outer diameter 170 at the proximal end 172 is greater than the outer diameter 170 at the distal end 174. In some cases, the outer diameter 170 at the distal end 174 is 0.035 inches. In other words, the dilator 152 is tapered toward the distal end 174.

The channel 156 extends through a portion of the dilator 152. The diameter 166 of the channel 156 in the dilator 152 can be constant along a longitudinal length of the channel 156. As the outer diameter 170 of the dilator 152 decreases from the proximal end 172 to the distal end 174, the height 168 of the channel 156 decreases. In some cases, the height 168 of the channel 156 decreases to zero at the distal end 174. In other cases, the height 168 of the channel 156 decreases to zero between the proximal end 172 and the distal end 174. In some cases, the height 168 of the channel 156 decreases at a rate less than the rate of the outer diameter 170 decreasing from the proximal end 172 to the distal end 174 of the dilator 152.

The dilator 152 and the stiffener 106 can be a polymer or a metal alloy. For example, the stiffener 106 can be polyurethane or medical grade alloy.

The guidewire 158 is a long thin wire used to guide the stiffener 106 and the catheter 104 to the abscess 102. In some procedures, the guidewire 158 can be inserted into the infected individual 126 (such as a mammalian subject) along a path from an exterior of the infected individual 126 to the abscess 102. The stiffener 106 and the catheter 104 can then be inserted along the guidewire 158 until distal ends 124 and 174 of the catheter 104 and the stiffener 106, respectively, are in the abscess 102. Then the guidewire 158 and the stiffener 106 can be removed, leaving the distal end 124 of the catheter 104 in the abscess 102. Then use of the catheter 104 can continue as described further herein. The guidewire 158 can be a metal. For example, the guidewire 158 can be a medical grade alloy. The guidewire 158 has an outer diameter 198. In some cases, the outer diameter 198 is 0.035 inches or 0.018 inches.

The catheter 104 has a hub 176 at the proximal end 122 coupled to the first tube 112 and the second tube 114. The hub 176 conducts the drainage (the flow) of the microbial organisms, infected tissue, and inflammatory biological material 116 out of the first lumen 108 and at the same time can conduct the flow (irrigation) of the medical fluid into the second lumen 110. The hub 176 has an inlet conduit 178 fluidly coupled to the second lumen 110 (the second lumen 110 inlet) and an outlet conduit 180 fluidly coupled to the coupled to the first lumen 108 (the first lumen 108 outlet).

The hub 176 has locks 182 to fasten the catheter 104 to the medical devices (described in detail in reference to FIG. 1E). As shown in FIG. 1A, the locks 182 can include multiple wire loops 184. In other implementations, as shown in FIGS. 1A and 1E, the locks 182 can include one or more Leur-locks 186.

In some cases, the proximal end 122 of the catheter 104 is capped. The inlet conduit 178 and the outlet conduit 180 can be capped. Alternatively or in addition, one or more of the Leur-locks 186 can be capped. The proximal end 122 of the catheter 104 can be capped to protect the proximal end 122 of the catheter 104, maintain cleanliness of the first and/or second lumen 108, 110, and/or prevent the flow through the first and/or second lumen 108, 110.

Referring to FIG. 1E, the system 100 for treating the abscess 102 can include a receiver 188 coupled to the hub 176 by a hose 190. The microbial organisms, infected tissue, and inflammatory biological material 116 drain from the abscess 102 into the first lumen 108 through the outlet conduit 180 and the hose 190 and into the receiver 188 in the direction of arrows 192. In some cases, the receiver 188 is a negative pressure source. For example, the negative pressure source can be a closed suction bulb, a disposable bag that drains by the force of gravity, a pump which provides suction (regular, variable, and/or intermittent), or a negative vacuum pressure provided by another source.

The system 100 can include an irrigation source 194 coupled to the hub 176 by another hose 190. The irrigation source 194 contains a medical fluid 196. The irrigation source 194 can flow the medical fluid 196 through the hose 190 into the inlet conduit 178 of the hub 176 through the second lumen 110 and into the abscess 102 to continuously irrigate the abscess 102. In some cases, the irrigation source 194 is an intravenous pump. The medical fluid 196 can be a saline solution, an antibiotic medicine, or a tissue plasminogen activase solution.

Continuously irrigating can include flowing the medical fluid 196 at a rate of between one and one hundred cubic centimeters per minute (cc/min) for a period of time. Such continuous irrigation can be performed while simultaneously draining the abscess 102. For example, the irrigation source 194 can flow the medical fluid 196 into the abscess 102 at a rate of five cc/min.

Figure 2:
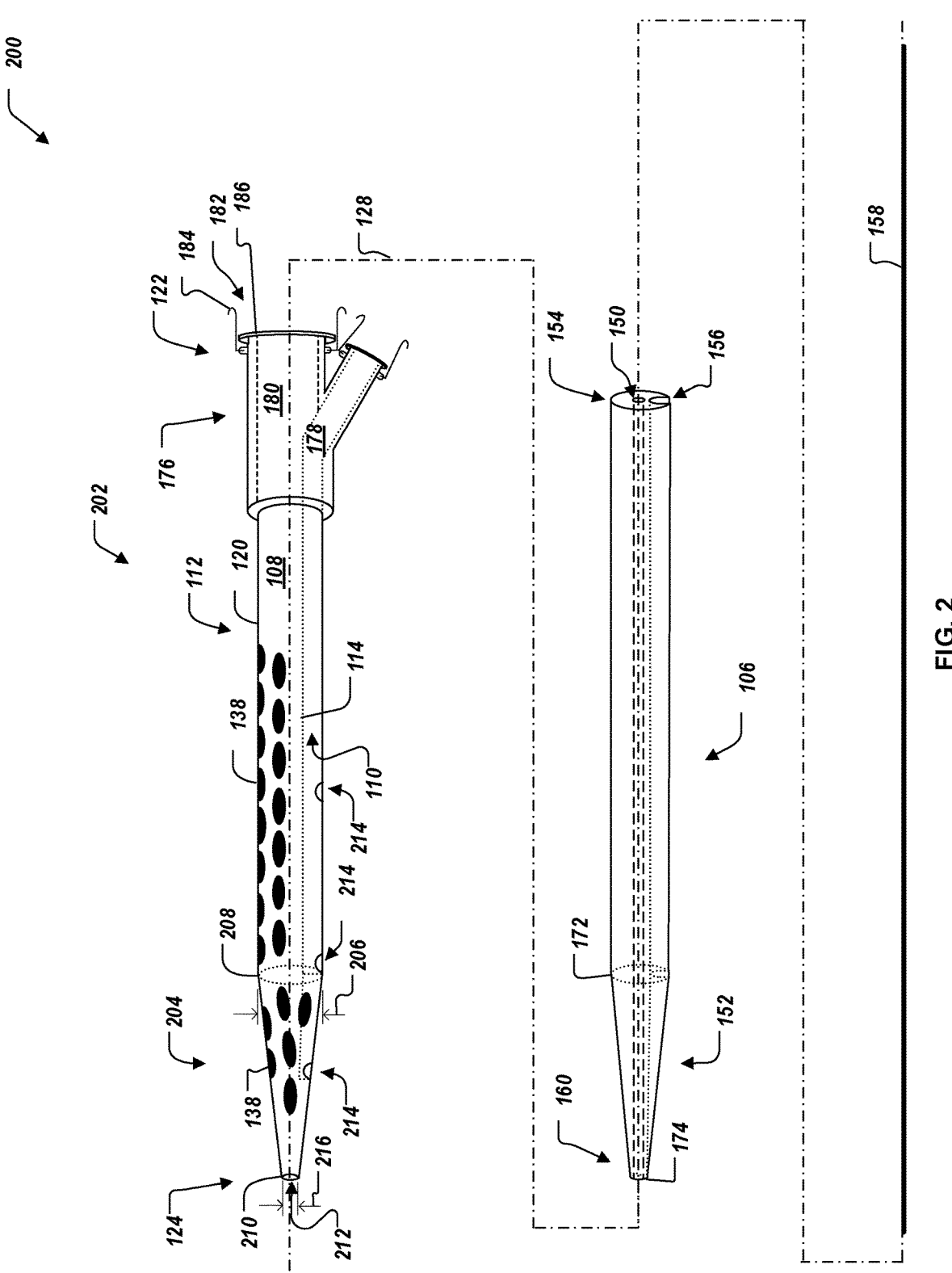
FIG. 2 is a schematic view of another system for continuously irrigating an abscess.

FIG. 2 is a schematic view of another system for continuously irrigating an abscess. A system 200 for continuously irrigating the abscess 102 (shown in FIG. 1D) of the infected individual 126 (also shown in FIG. 1D) includes a catheter 202 and the stiffener 106. The catheter 202 can be generally similar to the catheter 104 described in reference to FIGS. 1A-1E and can include one, several, or all of the features described with respect to the catheter 104.

The catheter 202 has a tapered tip 204 coupled to the first tube 112 and the second tube 114. The tapered tip 204 is coupled to the distal end 124 of the first tube 112 and the second tube 114. The tapered tip 204 extends from the first tube 112 and the second tube 114 toward the distal end 124. When the stiffener 106 is positioned in the catheter 104, the dilator 152 extends into and is positioned in the tapered tip 204.

The tapered tip 204 has an outer diameter 206. The tapered tip 204 has a first end 208 coupled to the first tube 112 and the second tube 114 and a second end 210 farther from the proximal end 122 along the center axis 128 than the first end 208. The outer diameter 206 of the first end 208 of the tapered tip 204 is the same as the outer diameter 132 of the first tube 112. The outer diameter 206 of the tapered tip 204 decreases between the first end 208 and the second end 210. That is, the outer diameter 206 at the second end 210 is less than the outer diameter 206 at the first end 208. The outer diameter 206 of the tapered tip can be between 0.035 and 0.42 inches. In other words, the tapered tip 204 is tapered toward the distal end 124.

The first lumen 108 of the catheter 202 extends through the tapered tip 204. An inlet 212 of the first lumen 108 is at the distal end 124 of the catheter 202. The microbial organisms, infected tissue, and inflammatory biological material 116 drain from the abscess 102 into the first lumen 108 through the inlet 212. The inlet 212 has an inner diameter 216. The inner diameter 216 can be between 0.018 and 0.035 inches (corresponding to just less the outer diameter 206, minus the thickness of the wall 140 of the first tube 112). In some cases, the inner diameter 216 at the second end 210 is 0.035 inches.

The catheter 202 includes the side holes 138 on the first tube 112. The side holes 138 of the catheter 202 can also be positioned on the tapered tip 204 to drain the microbial organisms, infected tissue, and inflammatory biological material 116 drain from the abscess 102 into the first lumen 108 through the side holes 138 of the tapered tip 204.

The catheter 202 includes one or more outlets 214 of the second lumen 110. The outlets 214 conduct the flow of the medical fluid from the second lumen 110 into the abscess 102 to continuously irrigate the abscess 102. The outlets 214 can be positioned along the first tube 112 between the proximal end 122 and the distal end 124 before the tapered tip 204. Alternatively or in addition, the outlets 214 can be positioned just before or at the first end 208 of the tapered tip 204. Alternatively, or in addition, the outlets 214 can be positioned along the tapered tip 204 between the first end 208 and the second end 210 of the tapered tip 204.

FIG. 3 is a schematic view of an abscess draining kit 300. The abscess draining kit 300 includes one or more of the systems, components, and features described in reference to FIGS. 1A-1E and FIG. 2. The abscess draining kit 300 includes the catheter 104 and the stiffener 106 described in reference to FIGS. 1A-1E. The abscess draining kit 300 can include multiple catheters 104 and the stiffeners 106 of the same or different sizes and/or lengths. In some cases, alternatively or in addition, the abscess draining kit 300 can include the catheter 202 described in reference to FIG. 2. The abscess draining kit 300 can include the guidewire 158.

The abscess draining kit 300 includes a catheter removal tool 302 to remove the catheter 104 after treatment of the abscess 102. The catheter removal tool 302 straightens the catheter 104 that has been placed in the abscess 102 as described in reference to FIGS. 1D-1E. The catheter removal tool 302 can be, for example, a suture mediated lock. For example, the catheter removal tool 302 can be a second stiffener 304 substantially similar to the stiffener 106 described in reference to FIGS. 1A-1E and FIG. 2.

The abscess draining kit 300 can include the receiver 188 described in reference to FIG. 1E to receive the microbial organisms, infected tissue, and inflammatory biological material 116 drained from the abscess 102 when the receiver 188 is coupled to the catheter 104. In some cases, the receiver 188 is a negative pressure source. For example, the negative pressure source can be a closed suction bulb, a gravity drain bag, or a suction-assisted bag.

The abscess draining kit 300 can include the irrigation source 194 coupled to the hub 176 by the hose 190. The irrigation source 194 contains the medical fluid 196. The irrigation source 194 can flow the medical fluid 196 through the hose 190 into the inlet conduit 178 of the hub 176 through the second lumen 110 and into the abscess 102 to continuously irrigate the abscess 102 when the irrigation source 194 is coupled to the catheter 104. In some cases, the irrigation source 194 is an intravenous pump. For example, the medical fluid 196 can be a saline solution, an antibiotic medicine, or a tissue plasminogen activase solution.

The abscess draining kit 300 can be used by the medical professional to place the catheter 104 in the abscess 102 and treat the abscess 102 by draining and continuously irrigating the abscess 102 as described in reference to FIGS. 1A-1E and FIG. 2 in a medical facility. When the medical professional has placed the catheter 104 in abscess 102 of the infected individual 126, and the abscess 102 can be drained with the receiver 188 coupled to the catheter 104 while the medical fluid 196 from the irrigation source 194 continuously irrigates the abscess 102.

In some cases, the irrigation source 194 can be disconnected from the catheter 104 while the abscess 102 is continuously drained into the receiver 188. In other cases, both the irrigation source 194 and the receiver 188 can be disconnected from the catheter 104, temporarily pausing treatment of the abscess 102. For example, when the infected individual 126 leaves the medical facility and returns home while the catheter 104 is still placed in the infected individual 126, one or both of the irrigation source 194 or the receiver 188 can be disconnected from the catheter 104. When the infected individual 126 arrives at home, the infected individual 126 can safely and easily reconnect one or both of the irrigation source 194 or the receiver 188 to the catheter 104 to resume treatment of the abscess 102 by draining and continuously irrigating the abscess 102 as described in reference to FIGS. 1A-1E and FIG. 2 at home. The infected individual 126 can safely and easily temporarily pause treatment of the abscess 102 by disconnecting one or both of the irrigation source 194 or the receiver 188 to leave home or return the medical facility for supervision by the medical professional.

FIG. 4 is a flow chart 400 of an example method of treating an abscess. At 402, a catheter, with a stiffener positioned in the catheter, is placed in an abscess, such as being inserted along a guidewire passing thought a guidewire passage of the stiffener. The stiffener is sized to fit inside a first lumen of the catheter. The stiffener defines a channel sized to fit a second lumen of the catheter positioned inside the first lumen such that a distal end of the stiffener can pass into and through the first lumen of the catheter with the second lumen positioned in the channel of the stiffener while the stiffener slides through the first lumen. For example, referring to FIGS. 1A and 1D, the stiffener 106 and the catheter 104 are positioned in the abscess 102. The channel 156 fits about the second tube 114.

At 404, after placing the catheter and the stiffener in the abscess, the stiffener and the guidewire are removed from the catheter. In some implementations, removing the stiffener from the catheter engages the catheter to the abscess. In some implementations, removing the stiffener from the catheter allows a distal portion of the catheter to relax from a substantially straight shape to a curved shape, such as forming a C-shape or a pig-tail shape. For example, referring to FIG. 1E, the portion 146 at the distal end 124 of the catheter 104 conforms to a C-shape to engage the catheter 104 in the abscess 102 when the stiffener 106 has been removed from the first lumen 108 of the catheter 104.

At 406, after removing the stiffener from the catheter, a pump is attached to a hub to flow a medical fluid to the second lumen and a closed suction bulb is attached to the hub to draw an abscess material into and through the first lumen. The hub is coupled to the first lumen and the second lumen to conduct the medical fluid into the second lumen and the abscess material into and through the first lumen. For example, referring to FIG. 1E, the irrigation source 194 (i.e., an intravenous pump) is coupled to the inlet conduit 178 of the hub 176 by locks 182. The receiver 188 (i.e., a closed suction bulb) is coupled to the outlet conduit 180 of the hub 176 by another locks 182.

At 408, the abscess is drained via the first lumen of the catheter. In some implementations, draining the abscess includes receiving an abscess material from a space exterior the first lumen through multiple voids into the first lumen. In some implementations, the closed suction bulb is operated to drain the abscess material from the abscess via the first lumen.

At 410, the abscess is continuously irrigated via the second lumen of the catheter while draining via the first lumen. In some implementations, a medical fluid is flowed out of a second lumen outlet of the second lumen to irrigate the abscess and one or more of the medical fluid and the abscess material is drawn into and through a first lumen inlet of the first lumen. Sometimes, the second lumen outlet and the first lumen inlet are coplanar. In some implementations, the pump is operated to continuously irrigate the abscess via the second lumen of the catheter while draining via the first lumen. For example, referring to FIG. 1E, the microbial organisms, infected tissue, and inflammatory biological material 116 (the abscess material) flow from the abscess 102 through the distal end 124 of the first lumen 108 (the inlet) and the side holes 138 into the first lumen 108 in the direction of arrows 192 and to the receiver 188.

At 412, operating the closed suction bulb is stopped to stop draining the abscess material from the abscess via the first lumen and operating the pump is stopped to stop irrigation of the abscess via the second lumen of the catheter while draining via the first lumen. For example, referring to FIG. 1E, the medical professional can stop operating the closed suction bulb (the receiver 188) and the intravenous pump (the irrigation source 194) can be stopped.

At 414, the pump and the closed suction bulb are detached from the hub. For example, the locks 182 can be actuated to remove the hoses 190 from the hub 176.

At 416, the catheter is removed from the abscess. In some implementations, the stiffener is a first stiffener, and removing catheter from the abscess includes inserting a second stiffener into the catheter. The second stiffener can be the same as the first stiffener or can be similar to the first stiffener with some differences. The second stiffener is sized to fit inside the first lumen. The second stiffener defines a second channel sized to fit the second lumen such that a distal end of the second stiffener can pass into and through the first lumen of the catheter with the second lumen positioned in the second channel of the second stiffener while the second stiffener slides through the first lumen. In some implementations, inserting the second stiffener into the catheter straightens the portion of the catheter. In some implementations, inserting the second stiffener into the catheter disengages the catheter from the abscess. For example, referring to FIGS. 3 and 1E, the second stiffener 304 can be placed in the first lumen 108 of the catheter 104 to straighten the C-shaped portion 146 of the catheter 104. The catheter 104 is disengaged from the abscess 102. The medical professional then removes the straightened catheter 104 and the second stiffener 304 from the infected individual 126.

Sometimes, treating the abscess is paused. After stopping operating the pump and the closed suction bulb, but before removing the catheter, the pump can be detached from the hub and the second lumen of the catheter can be plugged to prevent fluid flow through the second lumen of the catheter while draining the abscess via the first lumen. A second closed suction bulb can be attached to the hub to drain the abscess via the first lumen and the abscess is drained via the first lumen of the catheter to the closed suction bulb.

In some cases, when the second lumen has been plugged, the second lumen of the catheter can later be unplugged to again allow fluid flow through the second lumen of the catheter while draining the abscess via the first lumen. Sometimes, the pump can then be attached to flow the medical fluid to the hub and after attaching the pump to the hub, the closed suction bulb can be simultaneously operated to drain the abscess material from the abscess via the first lumen and operating the pump to continuously irrigate the abscess via the second lumen of the catheter while draining via the first lumen.

As used herein, the terms "aligned," "substantially aligned," or "approximately aligned" refer to an orientation of two elements (e.g., lines, axes, planes, surfaces, walls, or components) with respect to one and other that are in the same plane (i.e., co-planar) within acceptable engineering, machining, or measurement tolerances. For example, two surfaces can be considered aligned to each other if the angle between the surfaces is within an acceptable tolerance of zero degrees (e.g., ±1-5 degrees).

Although the detailed description contains many specific details for purposes of illustration, it is understood that one of ordinary skill in the art will appreciate that many examples, variations, and alterations to the following details are within the scope and spirit of the disclosure. For example, the size, shape and orientation of various features of the catheter and other components can be varied as suitable for the application. Accordingly, the example implementations described herein and provided in the appended figures are set forth without any loss of generality, and without imposing limitations on the claimed implementations.

Although the present implementations have been described in detail, it should be understood that various changes, substitutions, and alterations can be made hereupon without departing from the principle and scope of the disclosure. Accordingly, the scope of the present disclosure should be determined by the following claims and their appropriate legal equivalents.

The invention claimed is:

1. A system for draining an abscess, the system comprising:

a catheter having a first lumen and a second lumen; and a stiffener sized to fit inside the first lumen, wherein the stiffener defines:

a channel sized to fit the second lumen such that a distal end of the stiffener can pass into and through the first lumen of the catheter with the second lumen positioned in the channel of the stiffener while the stiffener slides through the first lumen; and a guidewire passage positioned at a center of a diameter defining the stiffener.

2. The system of claim 1, wherein the catheter defines a first lumen inlet at the distal end of the catheter, wherein the stiffener defines a dilator at the distal end of the stiffener, and wherein the stiffener is sized such that the dilator extends out of the first lumen inlet when the catheter and dilator are combined to be inserted into a patient.

3. The system of claim 2, wherein the second lumen further comprises a second lumen outlet at the distal end of the catheter, the first lumen inlet and the second lumen outlet are coplanar.

4. The system of claim 2, wherein the first lumen inlet is farther from a proximal end than a second lumen outlet.

5. The system of claim 2, wherein a second lumen outlet is farther from a proximal end than the first lumen inlet.

6. The system of claim 1, wherein the channel is defined along a perimeter edge of the stiffener.

7. The system of claim 1, wherein the second lumen is positioned inside the first lumen.

8. The system of claim 1, wherein the second lumen is coupled to an interior surface of the first lumen.

9. The system of claim 1, wherein a wall of the first lumen further comprises a plurality of side holes.

10. The system of claim 1, wherein the catheter further comprises a plurality of voids extending from the first lumen through an outer wall to a space exterior of the first lumen.

11. The system of claim 1, wherein the catheter further comprises:

a first lumen outlet at a proximal end of the catheter; and a second lumen inlet at the proximal end of the catheter.

12. The system of claim 11, further comprising a hub positioned at the proximal end of the catheter, the hub comprising:

an inlet conduit coupled to the second lumen inlet; and an outlet conduit coupled to the first lumen outlet.

13. The system of claim 1, wherein a portion at the distal end of the catheter conforms to at least one of a C-shape or a spiral shape responsive to a removal of the stiffener.

14. The system of claim 1, further comprising a tip coupled to and extending from the distal end of the first lumen, the tip narrowing to a diameter less than the diameter of the first lumen.

15. A system for draining an abscess, the system comprising:

a catheter sized and configured for percutaneous use in draining the abscess, the catheter defining a drainage lumen and an irrigation lumen;

a negative pressure source configured to be connected to the drainage lumen at a proximal end of the catheter;

an irrigation source configured to be connected to the irrigation lumen at the proximal end of the catheter, wherein the irrigation source is configured to irrigate the abscess while the negative pressure source operates to drain the abscess;

a stiffener sized to fit inside the drainage lumen about the irrigation lumen, the stiffener comprising a channel positioned at an outer diameter of the stiffener and configured to allow the channel of the stiffener to pass about the irrigation lumen as the stiffener passes into and through the drainage lumen, the stiffener comprising a guidewire passage positioned at a center of the outer diameter defined by the stiffener; and a guidewire configured to engage the guidewire passage to couple to the stiffener.

* * * * *